United States Patent [19]
Wofford et al.

[11] Patent Number: 5,860,939
[45] Date of Patent: Jan. 19, 1999

[54] METHOD FOR VERIFYING EFFICACY OF MANIPULATIVE THERAPY

[75] Inventors: Scott D. Wofford, Abilene, Tex.; Thomas J. Wright, Round Rock, Tex.

[73] Assignee: Jasao Corporation, Abilene, Tex.

[21] Appl. No.: 828,734

[22] Filed: Mar. 20, 1997

Related U.S. Application Data

[60] Provisional application No. 60/013,976 Mar. 21, 1996.
[51] Int. Cl.$^6$ .................................................. A61B 5/103
[52] U.S. Cl. ........................................... 600/587; 600/547
[58] Field of Search .................................... 600/544, 545, 600/547, 554, 587

[56] References Cited

U.S. PATENT DOCUMENTS

| | | | |
|---|---|---|---|
| 4,807,643 | 2/1989 | Rosier ...................................... | 600/554 |
| 5,313,956 | 5/1994 | Knutsson et al. ........................ | 600/545 |
| 5,388,587 | 2/1995 | Knutsson et al. ........................ | 600/545 |
| 5,656,017 | 8/1997 | Keller et al. ............................. | 601/108 |

OTHER PUBLICATIONS

*Evoked Potential Monitoring During Spinal Surgery,* Jeffrey H. Owen, 1991 (Chapter 3) (pp. 31–63).

*Predictability of Adequacy of Spinal Root Decompression Using Evoked Potentials,* Bernard Allan Cohen, PhD, Michael R. Mayor, MD, and Bernard A. Huizenga, MD (SP 380 Spine, vol. 16, No. 8 Supplement, 1991) (pp. S379–S384).

*Pathoanatomy and Pathophysiology of Nerve Root Compression,* Bjorn Rydevik, MD, Mark D. Brown, MD,† and Goran Lundborg, MD†, Mar. 16, 1983 (pp. 7–8).

*Dermatomal Somatosensory Evoked Potentials in the Diagnosis of Lumbosacral Spinal Stenosis: Comparison With Imaging Studies,* Mariol L. Snowden, MD, et al, Feb. 13, 1992 (pp. 1036–1044).

*Innervation Pattern of Dorsal Roots and Their Effects on the Specificity of Dermatomal Somatosensory Evoked Potentials,* Jeffrey H. Owen, Ph.D, et al, Spine, vol. 18, No. 6; Jul. 15, 1992 (pp. 748–754).

*Intraoperative Use of Dermatomal Somatosensory–evoked Potentials in Lumbar Stenosis Surgery,* Larry D. Herron, MD, et al, Central Coast Spine Institute, San Luis Obispo, CA; Spine, vol. 12, No. 14; 1987 (pp. 379–383).

*Mechanosensitivity of Dorsal Root Ganglia and Chronically Injured Axons: A Physiological Basis For the Radicular Pain of Nerve Root Compression,* John F. Howe, et al, Pain, 3 1977 Research Reports (pp. 25, 37–41).

*Dermatomal Somatosensory Evoked Potentials: Their Use in Lumbar Radiculopathy,* Victoria Dvonch, MD, et al, Spine, vol. 9, No. 3, 1984 Department of Orthopaedics & Rehabilitation; (pp. 291–293).

*The Electrodiagnostic Evaluation of Spinal Root Lesions,* Andrew Eisen, et al, Harper & Row, Publishers, Inc. 1983 Orthopaedic Associates of Milwaukee, S.C. & St. Michael Hospital (pp. 98–106).

*Dermatomal Monitoring for Surgical Correction of Spondylolisthesis A Case Report,* Bernard Allan Cohen, PhD, et al, May 30, 1988 (4 pages).

*Primary Examiner*—Max Hindenburg
*Assistant Examiner*—Charles Marmor, II
*Attorney, Agent, or Firm*—Baker & Botts, L.L.P.

[57] ABSTRACT

A method for objectively verifying the efficacy of manipulative therapy is provided. The method includes performing a first dermatomal somatosensory evoked potentials test [82] on a patient [12] to establish a baseline response of the nerve latency period. A manipulative therapy technique [88] is then performed on the patient to relieve nerve root compression. A second dermatomal somatosensory evoked potentials test [90] is then performed, to establish a post-manipulation nerve latency period.

29 Claims, 3 Drawing Sheets

OTHER PUBLICATIONS

*Somatosensory evoked potentials in the evaluation of lumbosacral radiculopathy,* David Walk, MD, et al, Jun. 1992 Neurology 42 (pp. 1197–1202).

*The Electrodiagnostic Evaluation of Nerve Root Function,* Scott Haldeman, MD, PhD, FRCP (C), Neurology Service, Veterans Administration Medical Center, Long Beach, and the Department of neurology, University of California, Irving, California, Mar. 16, 1983, (pp. 42–48).

*Dermatomal somatosensory evoked potentials: cervical, thoracic, and lumbosacral levels,* J. C. Slimp, D.E. Rubner, M. L. Snowden and W. C. Stolov, Department of Rehabilitation Medicine, University of Washington, Seattle, Washington Mar. 28, 1991 (pp. 55–69).

*New Approach for Diagnosis in Herniated Lumbosacral Disc,* Dermatomal Somatosensory, Evoked Potentials (DSSEPs), Masafumi Machida, MD, et al, Department of Orthopaedic Surgery Nihon University School of Medicine Tokyo, Japan and the Division of Clinical Electrophysiology, Department of Neurology University of Iowa Hospitals and Clinics, Iowa City, Iowa, Jun. 18, 1984 submitted for publication, Jan. 5, 1985 revised (pp. 380–384).

*Clinical Correlation Between Degenerative Spine Disease and Dermatomal Somatosensory–Evoked Potentials in Humans,* Jeffrey H. Owen, PhD, et al, Division of Orthopedic Surgery, Washington University School of Medicine, St. Louis, Missouri, and the Cleveland Spine Center, Cleveland, Ohio, Nov. 1, 1990 (pp. S 201–S205).

*Evaluation of the dermatomal somatosensory evoked potential in the diagnosis of lumbo–sacral root compression,* H. A. Katifi, E. M. Sedgwick, Wessex Neurological Centre, General Hospital, Southampton, UK, Journal of Neuroloty, Neurosurgery, and Psychiatry 1987;50: (pp. 1204–1210).

*Dermatomal Somatosensory Evoked Potentials in the Diagnosis of Lumbar Root Entrapment,* Timothy B. Scarff, MD, FACS, et al, Surgical Forum Neurological Surgery (pp. 489–491).

*The Value of Somatosensory Evoked Potential Testing for Upper Lumbar Radiculopathy,* A Correlation of Electrophysiologic and Anatomic Data, Jeffrey A. Saal, MD, et al, San Francisco Spine Institute, Daly City, California, Jan. 9, 1992 (pp. S133–S137).

*Somatosensory Evoked Potential from Dermotomal Stimulation as an Indicator of L5 and S1 Radiculopathy,* Arthur A1 Rodriquez, MD, Lorraine Kanis, MD, Arthur A. Rodriques, MD, Doylene Lane, BS, Arch. Phys. Med. Rehabil., vol. 68, Jun. 1987, pp. 366–368.

METHOD FOR VERIFYING EFFICACY OF MANIPULATIVE THERAPY

RELATED APPLICATIONS

This application claims the benefit of U.S. Provisional patent application Ser. No. 60/013976, "Dermatomal Somatosensory Evoked Potential Evaluation of Manipulative Medicine in the Treatment of Cervical and Lumbar Radiculopathy," filed Mar. 21, 1996, commonly owned and assigned with the present application.

TECHNICAL FIELD OF THE INVENTION

This invention relates to manipulative medicine in general and more particularly to a method for verifying the effectiveness of manipulative therapy using dermatomal somatosensory evoked potentials.

BACKGROUND OF THE INVENTION

Somatosensory Evoked Potential (SEP) tests have been employed for at least twenty years to monitor spinal cord function during surgical procedures. Surgical instrumentation or procedures may produce stress on the spinal cord. Repeated measurement of somatosensory evoked potentials during surgery provides electrophysiological data that may be used by the surgical team to make diagnostic decisions regarding global spinal cord function and nerve root trauma.

Nevertheless, somatosensory evoked potentials are not specific to individual nerve roots because they employ peripheral nerves that comprise nerve fibers that enter the spinal cord through several adjacent nerve roots. Consequently, somatosensory evoked potential wave forms are often not sufficiently specific to identify pathologies associated with individual nerve roots.

A Dermatomal Somatosensory Evoked Potential (DSEP) is produced by placing a stimulating surface electrode in a dermatomal field, such as an approved dermatome site, and recording the signature electrical response from scalp electrodes positioned on the head of a patient over the patient's somatosensory cortex. The evoked response to this peripheral stimulus theoretically can be used to evaluate the sensory input through individual sensory nerve roots.

Dermatomal somatosensory evoked potentials have been successfully employed to monitor spinal cord function during spinal surgery and to document successful spinal root decompression. Unlike somatosensory evoked potentials, the evoked response measured by the dermatomal somatosensory evoked potentials can be used to evaluate the sensory input through individual sensory nerve roots.

Patients with radicular pain often elect to pursue a conservative course of therapy that may initially include a combination of physical therapy and spinal manipulation. Such therapy may include the use of equipment such as the ACTIVATOR, or other similar equipment. Because the sensory components of nerve roots, especially the dorsal root ganglion, may be anatomically more vulnerable to mechanical or chemical pathology, patients may exhibit radicular pain and/or sensory loss without significant motor involvement. Although physical therapy and spinal manipulation may sometimes relieve these effects, no methods currently exist that may be used to correlate the resolution of problems with the performance of physical therapy using objective measurements.

SUMMARY OF THE INVENTION

Therefore a need has arisen for a method for evaluating the performance of a manipulative therapy that substantially eliminates or reduces disadvantages and problems associated with evaluating the performance of manipulative therapy.

In particular, a method for objectively evaluating the performance of manipulative therapy is required that eliminates the uncertainties associated with performing manipulative therapy to relieve radicular pain and/or sensory loss.

One aspect of the present invention is a method for objectively verifying the efficacy of manipulative therapy. The method includes performing a first dermatomal somatosensory evoked potentials test on a patient to establish a baseline response of the nerve latency period. A manipulative therapy technique is then performed on the patient to relieve nerve root compression at the affected segment. A second dermatomal somatosensory evoked potentials test is then performed, to establish a post manipulation nerve latency period.

The present invention provides many important technical advantages. One important technical advantage of the present invention is a method for evaluating the effectiveness of manipulative therapy using dermatomal somatosensory evoked potentials. The method of the present invention provides objective and repeatable results that particularly identify portions of the spine that may require manipulative therapy. In addition, the present invention may be used to verify the effectiveness of manipulative therapies.

DETAILED DESCRIPTION OF THE DRAWINGS

For a more complete understanding of the present invention and the advantages thereof, reference is now made to the following description taken in conjunction with the accompanying drawings in which like reference numbers indicate like features and wherein.

DETAILED DESCRIPTION OF THE INVENTION

Preferred embodiments of the present invention are illustrated in the figures, like numerals being used to refer to like and corresponding parts of the various drawings.

Figure 1:
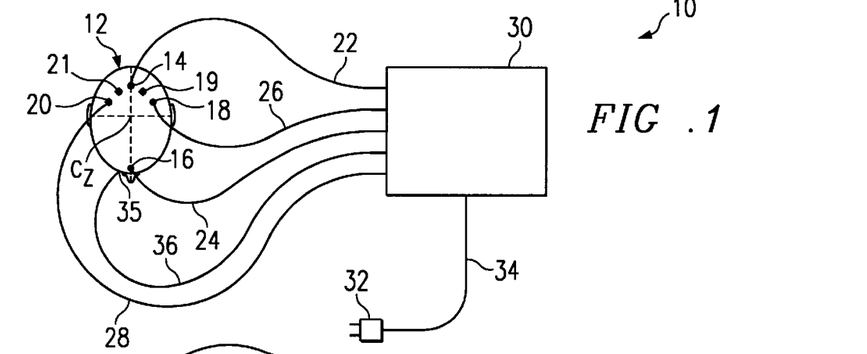
FIG. 1 is a diagram showing electrode placement on the head of a patient.

FIG. 1 is a diagram showing electrode placement on the head of a patient for use in performing dermatomal somatosensory evoked potentials tests in accordance with teachings of the present invention. Test setup 10 includes patient 12, standard 9 millimeter diameter disc electrodes 14, 16, 18, 19, 20, 21, and 35, conductors 22, 24, 26, 28, and 36, electrodiagnostic unit 30, stimulator electrode 32 and conductor 34. Electrodes 14, 16, 18, 19, 20, 21, and 35 are standard 9 millimeter diameter disc is electroencephalogram (EEG)-type recording electrodes, and are applied to predetermined recording sites on the scalp and head of the patient. Alternatively, electrodes 14, 16, 18, 19, 20, 21, and 35 may comprise other numbers of suitable electrodes.

In order to apply electrodes 14, 16, 18, 19, 20, 21, and 35 to the patient, the patient's skin at each of the recording sites is slightly abraded to provide a skin resistance of less than 5 ohms. Electrodes 14, 16, 18, 19, 20, 21, and 35 are then secured to the head of patient 12 with a self-adhering electrode cream. Electrodes 14, 18, 19, 20, and 21 are placed on the parietal scalp over the primary somatosensory areas in a coronal arc two centimeters posterior to $C_z$. $C_z$ is the point defined by the intersection of the line bisecting the left and right aural cavities and the line bisecting the patient's nose that extends across the top of the patient's head towards the base of the patient's skull.

Electrode 14 is positioned at $C_z'$, which is the point 2 centimeters posterior to $C_z$. Electrodes 18 and 20 are placed on an arc extending through the patient's right and left aural cavities at a point equal to 20 percent of the distance between the left and right aural cavity. Electrodes 19 and 21 are placed on an arc extending through the patient's right and left aural cavities at a point equal to 10 percent of the distance between the left and right aural cavity. Electrodes 18 and 20 may alternately be referred to as electrodes $C_3'$ (left) and $C_4'$ (right), respectively, and electrodes 19 and 21 may alternately be referred to as electrodes $C_1'$ (left) and $C_2'$ (right), respectively.

During a dermatomal somatosensory evoked potentials test, electrodes 18 and 20 will typically be used when nerve roots that extend through the cervical vertebrae are being tested. Electrodes 19 and 21 will typically be used when nerve roots that extend through the lumbar vertebrae are being tested.

Electrode 35 is placed on the chin or neck of patient 12 and is referenced to $F_z'$. Electrode 16 may also be referred to as $F_z'$. A ground electrode (not explicitly shown in FIG. 1) is placed on the chest of patient 12 at the manubrium. The ground electrode may also or alternatively be placed at other suitable sites. Standard skin abrasion and other techniques may be used to adhere the ground electrode to the patient.

Electrodes 14, 16, 18, 20, and 35 are coupled to electrodiagnostic unit 30 via conductors 22, 24, 26, 28, and 36, 34, respectively, thus forming a four channel dermatomal somatosensory evoked potentials study. Conductors 26 and 28 couple electrodes 18 and 20, respectively, to electrodiagnostic unit 30 when a cervical nerve root is being tested. Alternatively, conductors 26 and 28 may be used to couple electrodes 19 and 21, respectively, to electrodiagnostic unit 30 when a lumbar nerve root is being tested. Electrodes 14, 16, 18, 19, 20, 21, and 35 are standard 9 millimeter diameter disc electrode leads. Alternatively, other suitable numbers of channels and electrodes may be used. The number of channels typically varies between one and eight.

Conductors 22, 24, 26, 28, 34 and 36 may be copper conductors, coaxial conductors, twisted shielded conductor pairs, or other suitable conductors. Electrodiagnostic unit 30 comprises a multi-channel electric potential measuring device such as a MISTRAL, manufactured by TECA Corporation. Alternatively, electrodiagnostic unit 30 may comprise other suitable measuring devices. Conductors 26 and 28 couple to electrodes 18 and 20, respectively, when a cervical nerve root is being tested, and to electrodes 19 and 21, respectively, when a lumbar nerve root is being tested. Other nerve roots may also be tested where suitable, such as the thoracic or sacral nerve roots.

Electrodiagnostic unit 30 couples to stimulator electrode 32 via conductor 34, and is operable to apply a continuously variable controlled current for controlled predetermined durations. For example, electrodiagnostic unit 30 may be operable to apply a variable current signal comprising square wave pulses with a frequency of two to five hertz and an amplitude ranging from 0 to 50 milliamps for a duration of 0.1, 0.3 and 1 millisecond to stimulator electrode 32, and may be further operable to read voltages from electrodes 14, 16, 18, 19, 20, 21, and 35 at a sensitivity ranging from one microvolt per division to 5 millivolts per division. Alternatively, other suitable currents, voltages, waveforms, and frequencies may be used. Electrodiagnostic unit 30 is further operable to output a graph or other useful data derived from the voltages read at electrodes 14, 16, 18, 19, 20, 21, and 35, such as plotting a voltage at one electrode relative to the voltage at any other electrode.

In operation, stimulator electrode 32 is used to apply a stimulus to approved dermatome sites to stimulate nerves that project through cervical nerve roots bilaterally at C6, C7 and C8. For example, the nerve that projects through cervical nerve roots bilaterally at C6 may be stimulated by applying an electrical current to the thumb of patient 12, which is an approved dermatome site for the corresponding nerve. Likewise, an approved dermatome for the nerve that projects through the cervical nerve roots bilaterally at C7 is the middle finger, and an approved dermatome site for the nerve that projects through cervical nerve roots bilaterally at C8 is the fifth digit.

Applying an electrical current to these approved dermatomes stimulates the corresponding nerve. Stimulator electrode 32 may comprise a ring electrode when electrical current is applied to dermatomes on the patient's fingers or thumbs. Alternatively, other suitable dermatomes may be stimulated.

If testing is being performed to determine possible lumbosacral problems, stimulator electrode 32 may comprise a bar electrode with 9 millimeter disc electrodes fixed 3 centimeters apart. The dermatomes corresponding to nerves that project through the lumbosacral nerve roots bilaterally are then stimulated by application of an electric current to an approved corresponding dermatome site. For example, the medial calf, medial great toe, and dorsolateral foot are approved dermatome sites that correspond to the L4, L5 and S1 lumbosacral nerve roots.

For each dermatome, the sensory threshold is evaluated with 0.1 to 0.3 milliseconds square wave pulses applied at two to five hertz. The amplitude of the current is gradually increased until the sensory threshold for that patient is determined. Subsequent testing is performed at twice the sensory threshold with constant current square wave pulses. This level of stimulation produces an optimal evoked response while reducing both the patient's discomfort and the potential spread of the stimulus to adjacent dermatomes. Other levels of stimulation may also be used where suitable, including but not limited to stimulation below the sensory threshold. Likewise, other forms of stimulation, including but not limited to air and heat, may also be used where suitable.

The signals applied from stimulator electrode 32 cause a nerve response to be transmitted by the patient's nervous system to the patient's somatosensory cortex, thus causing nerve stimuli to be felt in the primary somatosensory areas. These nerve stimuli cause voltages to be generated at electrodes 14, 16, 18, 20, and 35. These generated voltages are transmitted to electrodiagnostic unit 30 by conductors 22, 24, 26, 28, and 36, respectively. In the case of testing a lumbar nerve root, conductors 26 and 28 would be attached to electrodes 19 and 21, respectively, and would transmit voltages generated at electrodes 19 and 21 to electrodiagnostic unit 30. Electrodiagnostic unit 30 then displays these measured voltages and records them for subsequent analysis. Typically, electrodiagnostic unit displays the voltages measured at electrodes 14, 18, 19, 20, and 21 relative to the voltage measured at electrode 16. This is typically referred to as a four channel dermatomal somatosensory evoked potentials test, since electrode 16 is used in conjunction with either electrodes 14, 18, and 20 or electrodes 14, 19, and 21.

By measuring the time difference between the application of a signal at stimulator electrode 32 until the measurement of a voltage response at electrodes 14, 16, 18, 19, 20, 21 and 35, it is possible to determine the time required for transmission of a nerve impulse signal through the body of patient 12 and to the cerebral cortex. The measured transmission times may then be used for several diagnostic purposes. One such diagnostic purpose is to determine the affected cervical or lumbosacral nerve region that requires manipulative therapy. A second diagnostic purpose is to compare the measured transmission time to a previously-measured transmission time taken before the performance of a manipulative therapy technique on the patient, in order to verify whether the manipulative therapy procedure was effective.

In general, the term manipulative therapy refers to any form of physical manipulation of a patient that is performed for the purpose or with the possible effect of relieving nerve root compression. Similar terms referring to such physical manipulation of a patient include, but are not limited to, physical therapy, spinal manipulation, adjustment, mobilization, or massage.

In addition, the measured transmission times may be used for a nondiagnostic purpose, such as to verify whether a particular manipulative therapy technique is effective. For example, a new manipulative therapy technique may be performed on a sample population of patients having a known cervical or lumbosacral condition. The measured transmission times for these patients before and after performance of the manipulative therapy technique may then be compiled and analyzed to determine whether the manipulative therapy technique was effective, or to determine potential alterations that may be made to the manipulative therapy technique to improve its effectiveness.

The second dermatomal somatosensory evoked potentials test may be performed at any time after manipulative therapy, including but not limited to immediately after manipulative therapy, several hours after manipulative therapy, or several days after manipulative therapy. Likewise, additional dermatomal somatosensory evoked potentials tests may be performed at these or other times to verify the status of the patient.

Figure 2:
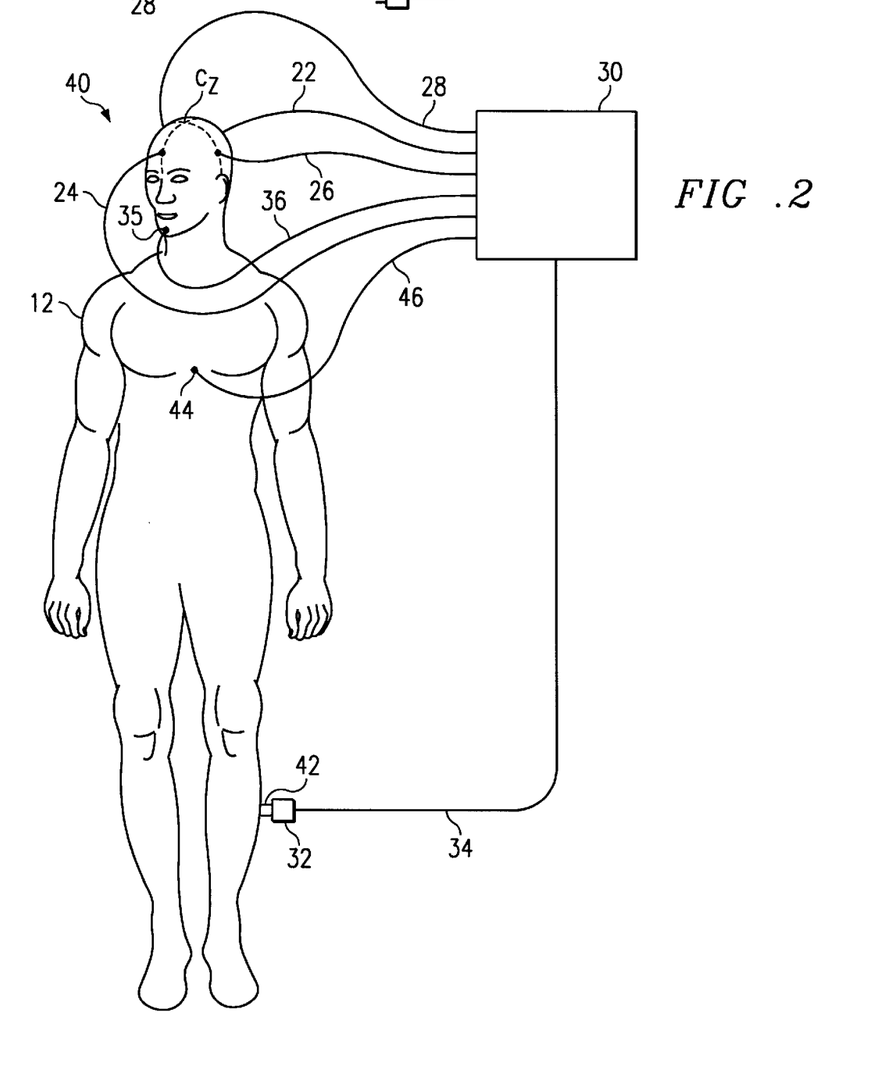
FIG. 2 shows connections between electrodes for a dermatomal somatosensory evoked potentials test and a patient.

FIG. 2 shows a frontal view of patient 12 while being tested by electrodiagnostic unit 30 in accordance with concepts of the present invention. Electrode 44 is applied to the chest of patient 12 and couples to electrodiagnostic unit 30 via conductor 46. Electrode 44 is a standard ground electrode disc EEG-type recording electrode, which is secured with self adhering electrode cream to the skin of patient 12. As previously noted, the skin of patient 12 may be lightly abraded to provide a skin resistance of less than 5 ohms.

Stimulator electrode 32 as shown in FIG. 2 is applied to the L4 dermatome 42 on the left-hand side of patient 12 at the medial calf. When an electric current is administered to L4 dermatome 42, a nerve impulse is generated that travels through the leg of patient 12 until it reaches the spinal column of patient 12. This nerve impulse enters the spinal column at the L4 lumbosacral nerve root and proceeds up through the spinal column of patient 12 until reaching the cerebral cortex. The nerve impulse is carried to the cerebral cortex, and generates a voltage at electrodes 14, 16, 19, 21, and 35 upon reaching the cerebral cortex.

Electrodiagnostic unit 30 measures the voltages at electrodes 14, 16, 19, 21, and 35, and uses the voltage from electrode 44 as a common voltage reference point (patient ground). The nerve signals generated by stimulator electrode 32 at the left-hand side L4 dermatome 42 will enter the right-hand side of the cerebral cortex, thus being detected by electrodes 14, 19, and 21.

If patient 12 is experiencing no nerve injury, the time required for transmission of the signal generated by application of stimulator electrode 32 should fall within normative values, and should be detected at electrodes 14, 16, 19, and 21. By plotting the signal received at electrodes 14, 16, 19, and 21 versus time, it is possible to determine the nerve impulse travel time, also known as the latency.

Figure 3:
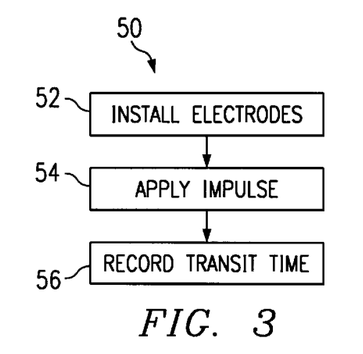
FIG. 3 is a flow chart of a method for performing a dermatomal somatosensory evoked potentials test embodying concepts of the present invention.

FIG. 3 is a flow chart of a method 50 for measuring dermatomal somatosensory evoked potentials for use in conjunction with manipulative therapy. The method of FIG. 3 is used repeatedly, at predetermined locations and at predetermined times, in accordance with teachings of the present invention. At step 52, electrodes are installed on a patient in a manner similar to that described above. At step 54, test signals, such as current impulses, are applied to standard dermatomes, such as the thumb for the C6 dermatome, the middle finger for the C7 dermatome, the fifth digit for the C8 dermatome, the medial calf for the L4 dermatome, the medial great toe for the L5 dermatome, and the dorsal lateral foot for the S1 dermatome.

The test signal applied at step 54 is initially calibrated to determine a sensory threshold. For example, if the test signal is a current impulse, the current may be applied at increasing magnitudes of current amplitude until a sensory threshold response is noted by the patient. Subsequent testing is then performed at a current impulse magnitude that is twice that of the sensory threshold of the patient, or at other suitable stimulatory levels.

Testing then continues by application of test signals and recording the corresponding transit time at step 56. For example, electrodiagnostic unit 30 is designed to measure the time difference between application of a test signal comprising a current impulse at dermatome 42 and measurement of a voltage response at electrodes 14, 16, 18, 19, 20, 21 and 35. This information is displayed to the user through a display of electrodiagnostic unit 30. Testing is completed when a set of measurements is taken that may be used to measure the transit time between the application of the test signal and the measurement of a voltage response at electrodes 14, 16, 18, 19, 20, 21, and 35.

Figure 4:
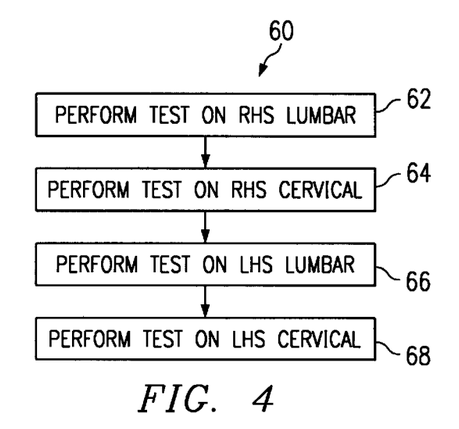
FIG. 4 is a flow chart of a method for performing a dermatomal somatosensory evoked potential test embodying concepts of the present invention.

FIG. 4 is a flow chart of a method 60 for performing a dermatomal somatosensory evoked potential test on a patient in conjunction with a manipulative therapy technique. At step 62, testing is performed on dermatomes corresponding to the right-hand side lumbar region of a patient. For example, as described above in order to determine the response of a patient, a bar electrode comprising two 9 millimeter disc electrode fixed three centimeters apart may be used to apply an electrical current impulse to the medial calf, medial great toe, and dorsal lateral foot nerves. The corresponding nerve impulse transit times are then measured in order to determine the state of the L4, L5 and S1 lumbosacral nerve roots.

At step 64, testing is performed on the right-hand side cervical nerve roots. For example, as described above in order to determine the response of a patient, a ring electrode may be used to apply an electrical current impulse to the thumb, middle finger, and fifth digit of the patient. The corresponding nerve impulse transit times are then measured in order to determine the state of the C6, C7 and C8 cervical nerve roots.

At step 66, testing is performed for the lumbar region on the left-hand side of the patient. Likewise, at step 68, testing is performed on the left-hand side of the patient for the cervical region. All of these tests may be made by a method for measuring dermatomal somatosensory evoked potentials similar to that shown in FIG. 3.

In operation, method 60 provides data that may be used to evaluate the dermatomal somatosensory evoked potential latency period, which is the transmission time required for a nerve impulse to reach the cerebral cortex of a patient from a dermatome region of the patient. These dermatomal somatosensory evoked potentials should follow known rules of physiological behavior. For example, impulses applied to the left-hand side of a patient should evoke a major response on the right-hand side of a patient. Likewise, the dermatomal somatosensory evoked potential latency period for the left-hand side dermatomes should be equal to that for the right-hand side dermatomes, absent any spinal injury or problems.

Figure 5:
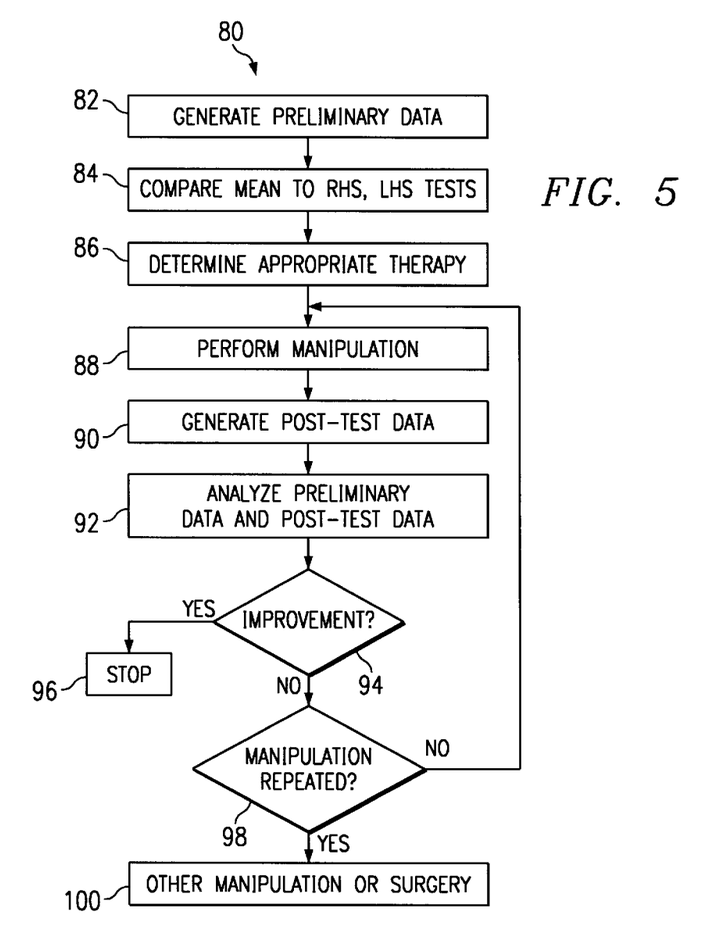
FIG. 5 is a method of using dermatomal somatosensory evoked potentials to verify the effectiveness of manipulative therapy embodying concepts of the present invention.

FIG. 5 is a flow chart of a method 80 for using dermatomal somatosensory evoked potentials to determine the efficacy of manipulative therapy procedures, embodying concepts of the present invention. At step 82, the preliminary dermatomal somatosensory evoked potential data for a patient is generated. For example, the preliminary data for the patient may be generated by performing a dermatomal somatosensory evoked potentials test using a method similar to that shown in FIGS. 3 and 4.

At step 84, the mean, right-hand side, and left-hand side tests results are compared. For example, data may be stored in electrodiagnostic unit 30 and may be superimposed or otherwise presented to the user in a manner that allows the user to determine the dermatomal somatosensory evoked potential latency period for each lumbar and cervical spinal segment. At step 86, the appropriate manipulative therapy technique, if any, is determined for the patient based upon the preliminary data. For example, if the data indicates a potential source of radicular pain in the lumbar region at the L5 vertebrae, a manipulative therapy technique may be chosen that will realign the L5 lumbar vertebrae, in order to relieve the impact on the lumbosacral nerve roots.

At step 88, the chosen manipulative therapy technique is performed to relieve any potential source of nerve compression. After completion of the manipulative therapy technique, the method proceeds to step 90. At step 90, post-test dermatomal somatosensory evoked potential data is compiled, such as by performing a dermatomal somatosensory evoked potentials test in accordance with a method similar to that shown in FIG. 4. At step 92, the results of post-test data and pre-test data are compiled and compared to determine whether the manipulative therapy performed at step 88 has been successful. For example, improvement may be shown by a decrease in the dermatomal somatosensory evoked potential latency period.

At step 94, it is determined whether there has been an improvement in the test data. For example, a pretreatment dermatomal somatosensory evoked potential test may have resulted in a latency period that exceeded two standard deviations of a normal response. If the post-treatment dermatomal somatosensory evoked potentials test results in a latency period that is within two standard deviations in a normal response, improvement is noted and manipulation therapy is stopped. The method then proceeds to step 95, and the patient is allowed to recuperate.

Otherwise, the method proceeds to step 98 and it is determined whether the manipulative therapy technique has been repeated. If manipulative therapy technique has not been repeated, it is possible that the manipulative therapy technique performed at step 88 was ineffective. The method then returns to step 88 and the manipulative therapy technique is performed again. If it is determined at step 98 that the manipulative therapy technique has been repeated, the method proceeds to step 100.

At step 100, a determination is made whether the manipulative therapy technique performed at step 88 may have been inadequate. As previously noted, method 80 may be used to evaluate a manipulative therapy technique, either to determine whether the technique is effective or to determine whether an improvement may be made to the technique. If it is determined at step 100 that the manipulative therapy technique applied at step 88 was not effective, this information may be used for a non-diagnostic purpose, such as to determine in conjunction with other similar data whether a particular manipulative therapy technique is effective for use with any patients.

Alternatively, a determination may be made at step 100 to perform additional manipulative therapy techniques, such as ones that manipulate other parts of the patient or ones that may provide the desired results under the existing conditions. Likewise, if several manipulative therapy techniques have been tried, and it appears that manipulative therapy is not resolving the problem, these results may be used to support a diagnosis to perform surgery.

Figure 6:
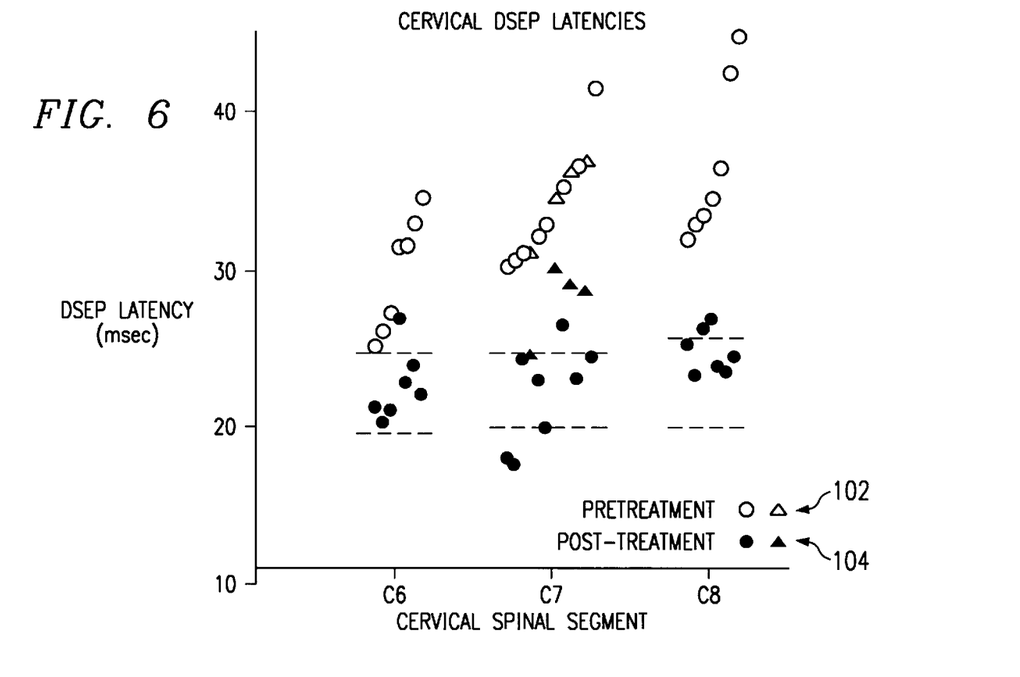
FIG. 6 is a graph of dermatomal somatosensory evoked potential latency as a function of cervical spine segment.

FIG. 6 is a graph of the results of actual pretreatment and post-treatment dermatomal somatosensory evoked potential latency as a function of cervical spinal segment for a sample population of patients. Icons 102 represent pretreatment dermatomal somatosensory evoked potentials measurements from patients that exhibited latency periods of greater than two times the standard deviation of normal healthy patients. Icons 104 represent the post-treatment dermatomal somatosensory evoked potential latency periods for the same group of patients after manipulative therapy. As can be seen in FIG. 6, the dermatomal somatosensory evoked potential latency periods are significantly different for the post-treatment group than for the pre-treatment group.

As can be seen from the results shown in FIG. 6, it is possible to determine whether a manipulative therapy technique has had a physiological effect on a patient's nerve impulse transmissions by measuring dermatomal somatosensory evoked potentials in conjunction with the performance of the manipulative therapy technique. These results demonstrate that the methods shown in FIG. 3 through FIG. 5 may be successfully used to determine the proper manipulative therapy based upon the suspected location of nerve root compression, and may also be used to determine the effectiveness of manipulative therapy techniques that are performed to relieve nerve root compression. Likewise, the methods shown in FIG. 3 through FIG. 5 may also be used to determine whether a new or experimental manipulative therapy technique is effective for relieving nerve root compression on patients with known nerve root compression problems.

Figure 7:
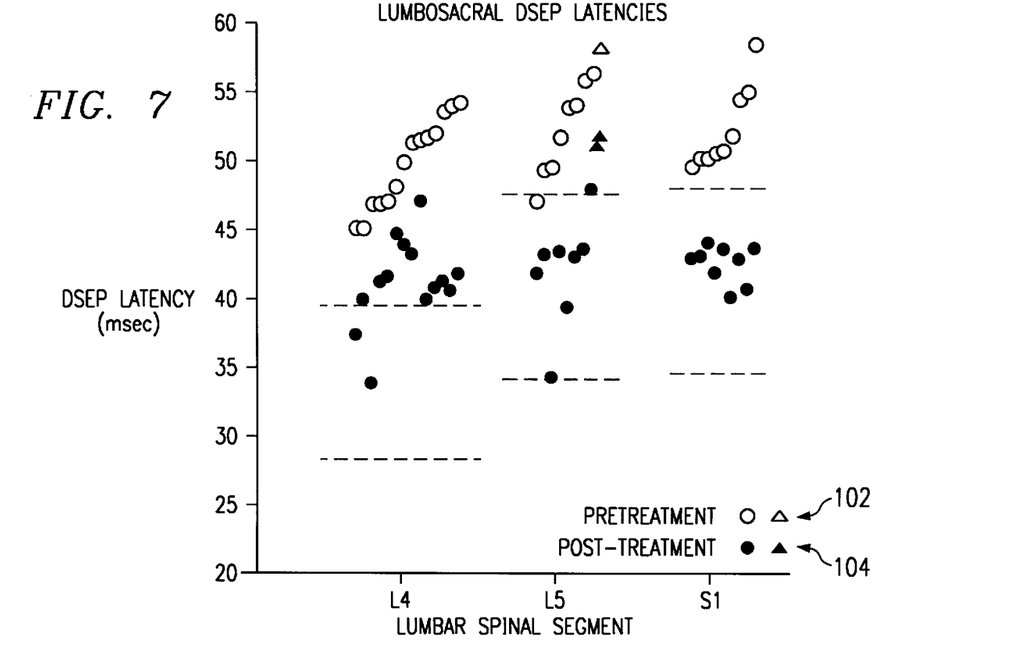
FIG. 7 is a graph showing dermatomal somatosensory evoked potential as a function of lumbar spine segment.

FIG. 7 is a chart showing the dermatomal somatosensory evoked potential latency period for the lumbar spinal segments. These measurements of dermatomal somatosensory evoked potentials, taken before and after the performance of manipulative therapy techniques, indicate that the latency period for nerve root compression by the L4 lumbar spinal segment did not improve after the performance of the manipulative therapy technique for the L4 lumbar spinal segment. These results are indicative of an ineffective manipulative therapy. Thus, the method of the present invention may be used to validate manipulative therapies, to determine whether such manipulative therapies are in fact decreasing the nerve impulse latency period.

In operation, dermatomal somatosensory evoked potentials are measured before performing a manipulative therapy technique to determine whether the nerve impulse latency period for nerve roots that enter the spinal cord of a patient is greater than a predetermined amount, such as two times the standard deviation of normal healthy patients. The manipulative therapy technique is then performed on the patient, and the dermatomal somatosensory evoked potentials are then measured again and compared to the initial results. A decrease in the nerve impulse latency period to within the predetermined amount may be used to infer successful completion of the manipulative therapy technique.

The present invention provides many important technical advantages. One important technical advantage of the present invention is a method for evaluating the effectiveness of manipulative therapy using dermatomal somatosensory evoked potentials. The method of the present invention provides objective and repeatable results that particularly identify portions of the spine that may require manipulative therapy. In addition, the present invention may be used to verify the effectiveness of manipulative therapies.

Although the present invention has been described in detail, it should be understood that various changes, substitutions, and alterations can be made hereto without departing from the spirit and scope of the invention as defined by the appended claims.

What is claimed is:

1. A method for verifying the efficacy of manipulative therapy comprising:

performing a first dermatomal somatosensory evoked potentials test on a patient to establish a baseline response;

performing a first nerve root compression relief manipulative therapy technique on the patient;

performing a second dermatomal somatosensory evoked potentials test on the patient to establish a post-manipulation response; and comparing the post-manipulation response to the baseline response.

2. The method of claim 1 wherein performing a first dermatomal somatosensory evoked potentials test further comprises performing a four channel dermatomal somatosensory evoked potentials test.

3. The method of claim 1 wherein performing a first dermatomal somatosensory evoked potentials test further comprises performing a dermatomal somatosensory evoked potentials test having a number of channels equal to one of one through eight channels.

4. The method of claim 1 wherein performing a first dermatomal somatosensory evoked potentials test further comprises:

placing a first electrode on a right side of a head of the patient;

placing a second electrode on a left side of the head of the patient;

placing a third electrode on a back side of the head of the patient;

placing a fourth electrode on a front side of the head of the patient; and placing a fifth electrode on one of a chin and a neck of the patient.

5. The method of claim 1 wherein performing a first dermatomal somatosensory evoked potentials test further comprises:

applying one or more test signals to the patient;

measuring a corresponding response voltage for each application of a test signal; and determining the time period between application of the test signal and measurement of the corresponding response voltage for each application of a test signal.

6. The method of claim 5 wherein applying one or more test signals further comprises applying the test signals to two or more dermatome sites.

7. The method of claim 5 wherein applying one or more test signals further comprises:

applying the test signals to two or more dermatome sites on the left-hand side of the patient; and applying the test signals to two or more dermatome sites on the right-hand side of the patient that correspond to the two or more dermatome sites on the left-hand side of the patient.

8. The method of claim 1 wherein performing a first nerve root compression relief manipulative therapy further comprises manipulating predetermined locations of the patient to cause movement of one or more spinal vertebrae so as to relieve any mechanical stress on one or more nerve roots of the patient.

9. The method of claim 1 wherein performing a second dermatomal somatosensory evoked potentials test further comprises performing a four channel dermatomal somatosensory evoked potentials test.

10. The method of claim 1 wherein performing a second dermatomal somatosensory evoked potentials test further comprises:

placing a first electrode on a right side of a head of the patient;

placing a second electrode on a left side of the head of the patient;

placing a third electrode on a back side of the head of the patient;

placing a fourth electrode on a front side of the head of the patient; and placing a fifth electrode on one of a chin and a neck of the patient.

11. The method of claim 1 wherein performing a second dermatomal somatosensory evoked potentials test further comprises:

applying one or more test signals to the patient;

measuring a corresponding response voltage for each application of the one or more test signals; and determining the time period between application of the test signal and measurement of the corresponding response voltage for each application of the test signal.

12. The method of claim 11 wherein applying one or more test signals further comprises applying the test signal to two or more dermatome sites.

13. The method of claim 11 wherein applying one or more test signals further comprises:

applying the test signals to two or more dermatome sites on the left-hand side of the patient; and applying the test signals to two or more dermatome sites on the right-hand side of the patient that correspond to the two or more dermatome sites on the left-hand side of the patient.

14. The method of claim 1 further comprising:

performing a second nerve root compression relief manipulative therapy on the patient if the post-manipulation response are not different from the baseline response; and performing a third dermatomal somatosensory evoked potentials test.

15. The method of claim 14 wherein performing a second nerve root compression relief manipulative therapy further comprises manipulating predetermined locations of the patient to cause movement of one or more spinal vertebrae so as to relieve any mechanical stress on one or more nerve roots of the patient.

16. The method of claim 1 wherein performing a first nerve root compression relief manipulative therapy on the patient further comprises:

determining a first nerve root compression relief manipulative therapy based upon the results of the first dermatomal somatosensory evoked potentials test; and performing the first nerve root compression relief manipulative therapy on the patient.

17. A method for verifying the effectiveness of a manipulative therapy technique comprising:

performing a first dermatomal somatosensory evoked potentials test on a patient to establish a baseline response;

performing a nerve root compression relief manipulative therapy technique on the patient;

performing a second dermatomal somatosensory evoked potentials test; and comparing the results of the first dermatomal somatosensory evoked potentials test to the results of the second dermatomal somatosensory evoked potentials test to determine whether the nerve root compression relief manipulative therapy technique caused a change in the dermatomal somatosensory evoked potentials test results.

18. The method of claim 17 wherein performing a first dermatomal somatosensory evoked potentials test further comprises performing a four channel dermatomal somatosensory evoked potentials test.

19. The method of claim 17 wherein performing a first dermatomal somatosensory evoked potentials test further comprises performing a dermatomal somatosensory evoked potentials test having a number of channels equal to one of one through eight channels.

20. The method of claim 17 wherein performing a first dermatomal somatosensory evoked potentials test further comprises:

placing a first electrode on a right side of a head of the patient;

placing a second electrode on a left side of the head of the patient;

placing a third electrode on a back side of the head of the patient;

placing a fourth electrode on a front side of the head of the patient; and placing a fifth electrode on one of a chin and a neck of the patient.

21. The method of claim 17 wherein performing a first dermatomal somatosensory evoked potentials test further comprises:

applying one or more test signals to the patient;

measuring a corresponding response voltage for each application of the test signal; and determining the time period between application of the test signal and measurement of the corresponding response voltage for each application of the test signal.

22. The method of claim 21 wherein applying one or more test signals further comprises applying the test signal to two or more dermatome sites.

23. The method of claim 21 wherein applying one or more test signals further comprises:

applying the test signals to two or more dermatome sites on the left-hand side of the patient; and applying the test signals to two or more dermatome sites on the right-hand side of the patient that correspond to the two or more dermatome sites on the left-hand side of the patient.

24. The method of claim 17 wherein performing a nerve root compression relief manipulative therapy further comprises manipulating predetermined locations of the patient to cause movement of one or more spinal vertebrae so as to relieve any mechanical stress on one or more nerve roots of the patient.

25. The method of claim 17 wherein performing a second dermatomal somatosensory evoked potentials test further comprises performing a four channel dermatomal somatosensory evoked potentials test.

26. The method of claim 17 wherein performing a second dermatomal somatosensory evoked potentials test further comprises:

placing a first electrode on a right side of a head of the patient;

placing a second electrode on a left side of the head of the patient;

placing a third electrode on a back side of the head of the patient;

placing a fourth electrode on a front side of the head of the patient; and placing a fifth electrode on one of a chin and a neck of a patient.

27. The method of claim 17 wherein performing a second dermatomal somatosensory evoked potentials test further comprises:

applying one or more test signals to the patient;

measuring a corresponding response voltage for each application of the test signal; and determining the time period between application of the test signal and measurement of the corresponding response voltage.

28. The method of claim 27 wherein applying one or more test signals further comprises the applying the test signal to two or more dermatome sites.

29. The method of claim 27 wherein applying one or more test signals further comprises:

applying the test signals to two or more dermatome sites on the left-hand side of the patient; and applying the test signals to two or more dermatome sites on the right-hand side of the patient that correspond to the two or more dermatome sites on the left-hand side of the patient.

* * * * *